(12) United States Patent
Umemoto et al.

(10) Patent No.: US 11,608,505 B2
(45) Date of Patent: Mar. 21, 2023

(54) GENOME-EDITED PLANT PRODUCTION METHOD

(71) Applicant: RIKEN, Wako (JP)

(72) Inventors: Naoyuki Umemoto, Wako (JP); Kazuki Saito, Wako (JP)

(73) Assignee: RIKEN, Wako (JP)

( * ) Notice: Subject to any disclaimer, the term of this patent is extended or adjusted under 35 U.S.C. 154(b) by 11 days.

(21) Appl. No.: 16/767,355

(22) PCT Filed: Nov. 21, 2018

(86) PCT No.: PCT/JP2018/042972
§ 371 (c)(1),
(2) Date: May 27, 2020

(87) PCT Pub. No.: WO2019/103034
PCT Pub. Date: May 31, 2019

(65) Prior Publication Data
US 2020/0385747 A1    Dec. 10, 2020

(30) Foreign Application Priority Data
Nov. 27, 2017    (JP) ............................. JP2017-226643

(51) Int. Cl.
*C12N 15/82*    (2006.01)

(52) U.S. Cl.
CPC ...... *C12N 15/8213* (2013.01); *C12N 15/8205* (2013.01); *C12N 15/8245* (2013.01)

(58) Field of Classification Search
CPC ......................... C12N 15/8213; C12N 15/8205
See application file for complete search history.

(56) References Cited

U.S. PATENT DOCUMENTS

| | | | |
|---|---|---|---|
| 5,965,791 | A | 10/1999 | Ebinuma et al. |
| 9,598,699 | B2 | 3/2017 | Umemoto et al. |
| 9,688,995 | B2 | 6/2017 | Umemoto et al. |
| 10,053,701 | B2 | 8/2018 | Umemoto |
| 10,138,491 | B2 | 11/2018 | Umemoto et al. |
| 2012/0159676 | A1 | 6/2012 | Umemoto et al. |
| 2015/0052635 | A1 | 2/2015 | Umemoto et al. |
| 2015/0284733 | A1 | 10/2015 | Umemoto |
| 2016/0222395 | A1 | 8/2016 | Stoddard et al. |
| 2017/0121727 | A1 | 5/2017 | Umemoto et al. |
| 2018/0016589 | A1 | 1/2018 | Gao et al. |
| 2018/0073035 | A1 | 3/2018 | Gao et al. |

FOREIGN PATENT DOCUMENTS

| | | | |
|---|---|---|---|
| JP | 9-154580 | A | 6/1997 |
| JP | 5794918 | B2 | 10/2015 |
| JP | 5902801 | B2 | 4/2016 |
| JP | 6038040 | B2 | 12/2016 |
| WO | 2016/116032 | A1 | 7/2016 |
| WO | 2016/119703 | A1 | 8/2016 |
| WO | 2016/125078 | A1 | 8/2016 |

OTHER PUBLICATIONS

Forsyth et al (Transcription Activator-Like Effector Nucleases (TALEN)-Mediated Targeted DNA Insertion in Potato Plants. Frontier in plant science. 7, 1-12, 2016) (Year: 2016).*
Chen et al (A simple method suitable to study de novo root organogenesis. Frontiers in Plant Science. 1-6, 2014) (Year: 2014).*
Zhang et al (Efficient and transgene-free genome editing in wheat through transient expression of CRISPR/Cas9 DNA or RNA. Nature communication. 7:12617, 1-8, 2016) (Year: 2016).*
Forsyth et al (Transcription Activator-Like Effector Nucleases (TALEN)-Mediated Targeted DNA Insertion in Potato Plants. Frontiers in Plant Science. 1-12, 2016) (Year: 2016).*
Hill et al (Enhancing plant regeneration in tissue culture. Plant Signaling & Behavior. 1-5, 2013). (Year: 2013).*
International Preliminary Report on Patentability, dated Jun. 2, 2020, issued by The International Bureau of WIPO in International Application No. PCT/JP2018/042972.
Report, The Current State and Issues of NPBT (New Plant Breeding Techniques), Aug. 26, 2014 (Heisei 26), the Science Council of Japan, Joint Working Group on Genetically Recombined Crops of Commission of Agriculture and Commission of Food Science, Joint Working Group on Breeding Science of Commission of Agriculture, Joint Working Group on Plant Science of Commission of Fundamental Biology Commission of Integrative Biology Commission of Agriculture.
Umemoto, Naoyuki et al., Genome editing for polyploid-and vegetative crop, potato, Agricultural Biotechnology, 2017, vol. 1 (1), pp. 22-27 (total 3 pages).
Butler, Nathaniel M. et al., Generation and Inheritance of Targeted Mutations in Potato (*Solanum tuberosum* L.) Using the CRISPER/Cas System, PLOS ONE, Dec. 14, 2015, 10, e0144591, pp. 1-12 (total 12 pages).
Ebinuma et al., Chemistry and Living Organism, 1997, vol. 35, No. 2, pp. 72-74 (total 3 pages).
Ebinuma, Hiroyasu, Development of a Transformation System for Woods, Japan Tapppo Journal, 1998, vol. 52, No. 1, pp. 72-76 (total 6 pages).
Forsyth et al., Transcription Activator-Like Effector Nucleases (TALEN)-Mediated Targeted DNA Insertion in Potato Plants, Frontiers in Plant Science, Oct. 25, 2016, vol. 7, Article 1572, pp. 1-12 (total 12 pages).
Srinivasan et al., Heterologous expression of the *Baby Boom AP2*/ERF transcription factor enhances the regeneration capacity of tobacco (*Nicotiana tabacum* L.), Planta, 2007, 225: pp. 341-351 (total 11 pages).
Heidmann et al., Pepper, Sweet (*Capsicum annuum*), Chapter 26, Methods in Molecular Biology, 2015, vol. 1223, pp. 321-334 (total 14 pages).

(Continued)

*Primary Examiner* — Charles Logsdon
*Assistant Examiner* — Wayne Zhong
(74) *Attorney, Agent, or Firm* — Sughrue Mion, PLLC

(57) ABSTRACT

It was found that it is possible to construct a genome-edited plant in which no exogenous gene is incorporated in a genome by performing negative selection using morphological defects and the like as indices in a regenerated plant originated from a plant cell in which a gene that induces regeneration of the plant and a gene of the genome editing enzyme are introduced.

4 Claims, 5 Drawing Sheets

Specification includes a Sequence Listing.

(56) References Cited

OTHER PUBLICATIONS

Lowe et al., Morphogenic Regulators *Baby boom* and *Wuschel* improve Monocot Transformation, The Plant Cell, Sep. 2016, vol. 28, pp. 1998-2015 (total 19 pages).
Altpeter et al., Advancing Crop Transformation in the Era of Genome Editing, The Plant Cell, Jul. 2016, vol. 28, pp. 1510-1520 (total 12 pages).
Banno et al., Overexpression of *Arabidopsis* ESR1 Induces Initiation of Shoot Regeneration, The Plant Cell, Dec. 2011, vol. 13, pp. 2609-2618 (total 11 pages).
Matsuo et al., *Arabidopsis* Enhancer of Shoot Regeneration 2 and *PINOID* are involved in in vitro shoot regeneration, Plant Biotechnology, 2012, vol. 29, pp. 367-372.
Sawai et al., Sterol Side Chain Reductase 2 Is a Key Enzyme in the Biosynthesis of Cholesterol, the Common Precursor of Toxic Steroidal Glycoalkaloids in Potato, The Plant Cell, Sep. 2014, vol. 26, pp. 3763-3774 (total 13 pages).
Umemoto et al., Two Cytochrome P450 Monooxygenases Catalyze Early Hydroxylation Steps in the Potato Steroid Glycoalkaloid Biosynthetic Pathway, Plant Physiology, Aug. 2016, vol. 171, pp. 2458-2467 (total 10 pages).
Nakayasu et al., A Dioxygenase Catalyzes Steroid 16α-Hydroxylation in Steroidal Glycoalkaloid Biosynthesis, Plant physiology, Sep. 2017, vol. 175, pp. 120-133 (total 14 pages).
Ma et al., Genome editing in potato plants by agrobacterium-mediated transient expression of transcription activator-like effector nucleases, Plant Biotechnol. Rep., Sep. 2017, vol. 11, pp. 249-258 (total 10 pages).
International Search Report for PCT/JP2018/042972 dated Feb. 19, 2019.

\* cited by examiner

```
Sayaka pSuehiro108 #127
TGGGGCTTCTTGTTTCAgctgaaatcaagcttATACCAGTTGATCAATA
TGGGGCTTCTTGTTTCAGCTGAAAT--AGCTTATACCAGTTGATCAATA
TGGGGCTTCTTGTTTCAGCTGAAAT--AGCTTATACCAGTTGATCAATA
TGGGGCTTCTTGTTTCAGCTGAAAT--AGCTTATACCAGTTGATCAATA
TGGGGCTTCTTGTTTCAGCTG------AGCTTATACCAGTTGATCAATA
TGGGGCTTCTTGTTTCAGCTG------AGCTTATACCAGTTGATCAATA
TGGGGCTTCTTGTTTCAGCTG------AGCTTATACCAGTTGATCAATA
TGGGGCTTCTTGTTTCAGCTG------AGCTTATACCAGTTGATCAATA
TGGGGCTTCTTGTTTCAGCTG------AGCTTATACCAGTTGATCAATA
TGGGGCTTCTTGTTTCAGCTG------AGCTTATACCAGTTGATCAATA
TGGGGCTTCTTGTTTCAGCTGA-------CTTATACCAGTTGATCAATA
TGGGGCTTCTTGTTTCAGCTGA-------CTTATACCAGTTGATCAATA
TGGGGCTTCTTGTTTCAGCTGA-------CTTATACCAGTTGATCAATA
TGGGGCTTCTTGTTTCAGC-----------TTATACCAGTTGATCAATA
TGGGGCTTCTTGTTTCAGC-----------TTATACCAGTTGATCAATA
TGGGGCTTCTTGTTTCAGC-----------TTATACCAGTTGATCAATA pSuehiro108 #164
TGGGGCTTCTTGTTTCAgctgaaatcaagcttATACCAGTTGATCAATA
TGGGGCTTCTTGTTTCAGCTG--------CTTATACCAGTTGATCAATA
TGGGGCTTCTTGTTTCAGCTG--------CTTATACCAGTTGATCAATA
TGGGGCTTCTTGTTTCAGC-----------TTATACCAGTTGATCAATA
TGGGGCTTCTTGTTTCAGC-----------TTATACCAGTTGATCAATA
TGGGGCTTCTTGTTTCAGC-----------TTATACCAGTTGATCAATA
TGGGGCTTCTTGTTTCAGC-----------TTATACCAGTTGATCAATA
------------(200 bp del)-------------------------
------------(200 bp del)-------------------------
------------(200 bp del)-------------------------
------------(200 bp del)-------------------------
------------(200 bp del)-------------------------
------------(200 bp del)-------------------------
------------(200 bp del)-------------------------
------------(200 bp del)-------------------------
------------(200 bp del)-------------------------
```

Fig. 5

```
Mayqueen pSuehiro114 #15
TGGGGCTTCTTGTTTCAgctgaaatcaagcttATACCAGTTGATCAATA
TGGGGCTTCTTGT--( 111 bp del + 52 bp ins )--------
TGGGGCTTCTTGT--( 111 bp del + 52 bp ins )--------
TGGGGCTTCTTGT--( 111 bp del + 52 bp ins )--------
TGGGGCTTCTTGT--( 111 bp del + 52 bp ins )--------
TGGGGCT--------( 64 bp del + 34 bp ins )--------
TGGGGCT--------( 64 bp del + 34 bp ins )--------
TGGGGCT--------( 64 bp del + 34 bp ins )--------
-----( 122 bp del + 15 bp ins )-------GTTGATCAATA
-----( 122 bp del + 15 bp ins )-------GTTGATCAATA
-----( 122 bp del + 15 bp ins )-------GTTGATCAATA
-----( 122 bp del + 15 bp ins )-------GTTGATCAATA
-----( 122 bp del + 15 bp ins )-------GTTGATCAATA
-----( 122 bp del + 15 bp ins )-------GTTGATCAATA
```

GENOME-EDITED PLANT PRODUCTION METHOD

CROSS REFERENCE TO RELATED APPLICATIONS

This application is a National Stage of International Application No. PCT/JP2018/042972, filed Nov. 21, 2018, claiming priority based on Japanese Patent Application No. 2017-226643, filed Nov. 27, 2017.

TECHNICAL FIELD

The present invention relates to a method for producing a genome-edited plant in which a mutation is introduced in a specific gene on a genome and no exogenous gene is incorporated in the genome and to a genome-edited plant produced by the method.

BACKGROUND ART

The genome editing technologies are technologies that introduce a mutation into a site targeted by a target gene utilizing a genome editing enzyme. As the genome editing enzyme, ZFNs (Zinc Finger Nucleases), TALENs (Transcription Activator Like Effector Nucleases), and CRISPR-Cas9 (Clustered Regularly Interspaced Short Palindromic Repeats CRISPR-Associated Proteins 9) were developed in the early 2000's, 2010, and 2012, respectively.

Conventionally, in the construction of a plant having a target mutation, the Tilling method which selects a plant in which a target gene is destroyed from a pool of mutants, and the like have been utilized. However, utilizing the genome editing technologies has made it possible to promptly obtain a target plant as compared with the conventional methods and also to avoid influence (mutation) on genes other than the target gene. In addition, since plants obtained by the genome editing technologies cannot be distinguished from mutants obtained by the conventional method, it is expected that such plants are not strictly regulated at the same level as for genetically modified plants. For these advantages, the genome editing technologies are attracting lots of attention also as novel plant breeding technologies (NPL 1).

In animals, it is possible to easily obtain a genome-edited plant by introducing a genome editing enzyme in the form of RNA, protein, or complex into a fertilized egg without incorporating the gene of the genome editing enzyme into the genome. On the other hand, in plants, since it is difficult to obtain a fertilized egg, a genome editing enzyme is introduced in the form of RNA, protein, or complex into an isolated cell or protoplast. By regenerating a plant from the cell or protoplast manipulated as described above, a genome-edited plant in which the gene of the genome editing enzyme is not incorporated in the genome has been successfully obtained. However, the species and cultivars that can be regenerated from protoplasts and the like are limited, and many culture mutations are likely to be generated in the course of regeneration from protoplasts, there is a problem that there is a limitation on the range of application of this approach.

In addition, in the case of plants that are easily self-fertilized and plants whose cultivars are constructed in the course of hybridization such as self-fertilization, it is possible to obtain plants in which the gene of the genome editing enzyme is not incorporated in the genome in the end by removing the gene through hybridization after incorporating the gene of the genome editing enzyme into the genome. However, in the case of a crop such as potato whose elite cultivar is maintained through vegetative propagation, once the crop is hybridized with the constructed elite cultivar, the crop is changed to a cultivar different from the original cultivar. For this reason, there is a problem that a method for removing the gene of the genome editing enzyme incorporated in the genome by hybridization is not so useful (NPL 2). A method for expressing a genome editing enzyme from a geminivirus vector that is not incorporated into the genome of a plant has also been reported (NPL 3). However, in order to overcome restrictions as a plant having no sign of genetic recombination, it is considered that the removal of the virus and the proof of the removal are necessary.

For this reason, there is a demand for a novel method for obtaining a genome-edited plant in which a mutation is introduced into a specific gene on the genome without an exogenous gene being incorporated into the genome.

Meanwhile, the ipt gene from *Agrobacterium* is known to contribute to the syntheses of plant hormones. It is possible to obtain a marker-free mutant by incorporating this gene into the genome of a plant once and removing the gene from the obtained recombinant (multiple shoot) to elongate without defects (MAT vector method; NPL 4). In addition, it is known that the transformation efficiency is improved in a plant that is difficult to transform by utilizing the ipt gene (NPL 5). Moreover, the case in which the ipt gene was used as a negative selection marker in the introduction of an exogenous gene through homologous recombination was also reported (NPL 6).

It has been reported that the bbm (Baby Boom) genes of *Arabidopsis thaliana* and *Brassica napus* have activities such as enhancement of the regeneration ability in tobacco (NPL 7), promotion of the transformation in chili pepper (NPL 8), and enhancement of the transformation in monocot (NPL 9). In addition, it has been reported that ESR1 and ESR2 of *Arabidopsis thaliana* promotes the regeneration of the shoots (NPLs 11 and 12). Besides these, the gene that promotes transformation in genome editing has also been reported (NPL 10).

However, there is no report regarding utilizing these genes in order to select a genome-edited plant in which a mutation is introduced into a specific gene on a genome without an exogenous gene being incorporated on the genome.

Potato is a food crop that has the fourth-largest world production. Potato that has taken on green as a result of exposure to light and portions of potato sprouts contain large amounts of components called steroidal glycoalkaloids such as solanine. These components are known to cause bad taste in small amount and cause poisoning in large amount. For this reason, the elimination of the poison of potato has been a large problem as the food crop and the technical development for this problem has been in progress.

For example, it has been reported that a plant with reduced steroidal glycoalkaloids can be obtained by knocking down the SSR2 gene through transformation or genome-editing the SSR2 gene (PTL 1 and NPL 13). Similarly, it has also been reported that in order to obtain a plant with reduced steroidal glycoalkaloids, the PGA1 gene or the PGA2 gene (NPL 14), the 16DOX gene (NPL 15), the E gene (PGA3 gene) (PTL 2), and the Y gene (PGA4 gene) (PTL 3) are knocked down through transformation.

However, in order to knock down the target gene through transformation, it is necessary to perform genetic recombination. In addition, in the plant with reduced steroidal glycoalkaloids by genome editing reported in the example of the SSR2 gene, the character of the cultivar can be maintained in the genetically recombined state. On the other hand, removing the genome editing tool requires hybridization, and in this case, there is a problem that the cultivar cannot be maintained.

As described above, all of the conventional constructions of plants with reduced steroidal glycoalkaloids have problems resulting from exogenous genes being incorporated into the genomes.

CITATION LIST

Patent Literature

[PTL 1] Japanese Patent No. 5902801
[PTL 2] Japanese Patent No. 5794918
[PTL 3] Japanese Patent No. 6038040

Non Patent Literature

[NPL 1] REPORT, The Current State and Issues of NPBT (New Plant Breeding Techniques), Aug. 26, 2014 (Heisei 26), the Science Council of Japan, Joint Working Group on Genetically Recombined Crops of Commission of Agriculture and Commission of Food Science, Joint Working Group on Breeding Science of Commission of Agriculture, Joint Working Group on Plant Science of Commission of Fundamental Biology•Commission of Integrative Biology•Commission of Agriculture
[NPL 2] Umeki et al., (2016) Agribio 1: 21-25
[NPL 3] Nathaniel et al., (2015) PLoS ONE 10: e0144591
[NPL 4] Ebinuma et al., (1997) Chemistry and Living Organism 35: 72-74
[NPL 5] Ebinuma, (1998) Japan TAPPI Journal 52: 72-76
[NPL 6] Forsyth et al., (2016) Front Plant Sci. 7: 1572
[NPL 7] Srinivasan et al., (2007) Planta 225: 341-351
[NPL 8] Heidmann & Boutilier (2015) Methods Mol Biol. 1223: 321-34
[NPL 9] Lowe et al., (2016) Plant Cell 28: 1998-2015
[NPL 10] Altpeter et al., (2016) Plant Cell 28: 1510-1520
[NPL 11] Banno et al., (2001) Plant Cell 13: 2609-2618
[NPL 12] Matsuo et al., (2012) Plant Biotechnol. 29: 367-372
[NPL 13] Sawai et al., (2014) Plant Cell 26: 3763-3774
[NPL 14] Umemoto et al., (2016) Plant Physiol. 171: 2458-2467
[NPL 15] Nakayasu et al., (2017) Plant Physiol. 175: 120-133

SUMMARY OF INVENTION

Technical Problem

The present invention has been made in view of the above-described problems of the conventional techniques, and an object thereof is to provide a novel method capable of editing the genome of a plant without incorporating an exogenous gene into the genome.

Solution to Problem

In general, in the case of regenerating a plant from a plant tissue, the plant tissue is cultured in a growth medium containing plant hormones (auxin and cytokinin) in appropriate concentrations. It is possible to regenerate a plant from a plant tissue in a growth medium that contains no plant hormones by transiently expressing isopentenyltransferase (ipt), which catalyzes the rate-limiting reaction of cytokinin biosynthesis. On the other hand, it is also known that in a tissue expressed constitutively by incorporating ipt in the genome, morphological defects are caused, and in many cases, forms similar to multiple shoot in which the internode is narrowed and calli are caused (NPL 4).

From these facts, the present inventor considered that if there is a plant that is transiently expressed without the ipt gene being incorporated in the genome among plants regenerated by introducing the ipt gene, a target genome-edited plant might be obtained by eliminating plants in which the ipt gene is incorporated in the genome (that is, performing negative selection) using morphological defects as indices.

Based on this concept, the present inventor first constructed a vector that holds the ipt gene as a gene that induces regeneration of a plant and the TALENs gene as a gene of the genome editing enzyme. In addition, the present inventor selected a gene (SSR2 gene) coding a steroidal glycoalkaloid biosynthesis enzyme as an example of the target gene of TALENs. Subsequently, the present inventor introduced the vector into potato, which is representative of crops whose elite cultivars are maintained through vegetative propagation, by the *Agrobacterium* method, followed by culturing in a growth medium that did not contain plant hormones to obtain regenerated plants. The present inventor then analyzed the genomes of the obtained regenerated plants and found that genome-edited plants that did not exhibit morphological defects were also generated besides genome-edited plants that exhibited morphological defects. While the exogenous gene was incorporated in the genomes of all the plants that exhibited morphological defects, the exogenous gene was not incorporated in the genome of the genome-edited plants that did not exhibit morphological defects.

The present inventor further investigated other multiple genes that induce regeneration of a plant and was able to obtain genome-edited plants in which the exogenous gene was not incorporated in the genomes like the ipt gene.

From the above-described facts, the present inventor found that it is possible to obtain a genome-edited plant in which the exogenous gene is not incorporated in the genome by removing plants in which the exogenous gene is incorporated in the genome using morphological defects and the like as indices from regenerated plants originated from plant cells in which a gene that induces regeneration of the plant and a gene of a genome editing enzyme. This finding has led to the completion of the present invention. More specifically, the present invention provides as follows:

[1] A method for producing a genome-edited plant in which a mutation is introduced into a specific gene on a genome and no exogenous gene is incorporated in the genome, comprising the steps of:

(a) introducing a construct that expresses a gene encoding a genome editing enzyme targeting the specific gene on the genome and a gene encoding a protein that induces or promotes regeneration of a plant into a plant cell;

(b) culturing the plant cell obtained in the step (a) and selecting a regenerated plant; and (c) selecting a plant in which the gene encoding a genome editing enzyme and the gene encoding a protein that induces or promotes regeneration of a plant are not incorporated in the genome from the plant selected in the step (b).

[2] The method according to [1], wherein
the introduction of the construct into a plant cell in the step (a) is conducted by an *Agrobacterium* method.

[3] The method according to [1] or [2], wherein
the culturing of the plant cell in the step (b) is conducted in a growth medium that contains no plant hormones.
[4] The method according to any one of [1] to [3], wherein in the step (c), a plant in which no morphological defect has occurred is selected.
[5] The method according to any one of [1] to [4], wherein the gene encoding a protein that induces or promotes regeneration of a plant is a gene selected from the group consisting of an ipt gene, a bbm gene, an ESR1 gene, an ESR2 gene, a LEC2 gene, and a WUS gene.
[6] A genome-edited plant produced by the method according to any one of [1] to [5].
[7] A genome-edited plant having (a) to (c) characteristics as follows:
(a) a mutation is introduced in a specific gene on a genome by a genome editing enzyme;
(b) no exogenous gene is incorporated on the genome; and
(c) the genome-edited plant is not hybridized after the editing of the genome by the genome editing enzyme.
[8] The genome-edited plant according to [7], wherein the genome-edited plant is a plant having a vegetatively propagated cultivar.
[9] The genome-edited plant according to [8], wherein the genome-edited plant is potato.
[10] The genome-edited plant according to [9], wherein a mutation is introduced in a gene encoding a steroidal glycoalkaloid biosynthesis enzyme by the genome editing enzyme.
[11] The genome-edited plant according to [10], wherein accumulation of steroidal glycoalkaloids is reduced.

Advantageous Effects of Invention

Conventionally, in selecting a target plant utilizing a gene such as the ipt gene that induces regeneration of a plant, an approach has been used in which plants that exhibit morphological defects due to constitutive expression of the gene are selected (that is, positive selection is performed), the gene is removed to allow the plants to recover from the morphological defects (NPL 4). In contrast, the method of the present invention performs negative selection of a plant that constitutive expresses the gene, and thus is a breakthrough method with completely different ideas from the conventional methods. The present invention makes it possible to perform genome editing on a plant without incorporating an exogenous gene such as a gene encoding a genome editing enzyme into the genome. Hence, the present invention can be utilized as a fundamental technology for performing genome editing while maintaining the identity of the cultivar in plants that require vegetative propagation from the viewpoint of cultivar maintenance and the like. For example, if genome editing according to the present invention is performed on a gene encoding steroidal glycoalkaloid biosynthesis enzyme of potato, it is possible to obtain potato whose cultivar's character is maintained, at the same time in which a mutation has occurred in all allele but a mutation has not occurred in the other genes, and which has a very low content of steroidal glycoalkaloid.

BRIEF DESCRIPTION OF DRAWINGS

FIG. 3 shows a result of alignment between a nucleic acid sequence (the first row) near a target sequence for genome editing in the SSR2 gene of the potato cultivar "Sassy" and nucleic acid sequences (the second row and after) of amplified fragments containing genome-edited regions cloned from genome-edited plants. "-" indicates deletion, and the number of deleted bases are described for deleted sequences exceeding the region.

FIG. 4 shows a result of alignment between a nucleic acid sequence (the first row) near a target sequence for genome editing in the SSR2 gene of the potato cultivar "Sayaka" and nucleic acid sequences (the second row and after) of amplified fragments containing genome-edited regions cloned from genome-edited plants. "-" indicates deletion, and the number of deleted bases are described for deleted sequences exceeding the region.

FIG. 5 shows a result of alignment between a nucleic acid sequence (the first row) near a target sequence for genome editing in the SSR2 gene of the potato cultivar "May Queen" and nucleic acid sequences (the second row and after) of amplified fragments containing genome-edited regions cloned from genome-edited plants. "-" indicates deletion, and the number of deleted bases and the number of added bases are described for deleted sequences and added sequences exceeding the region.

DESCRIPTION OF EMBODIMENTS

Figure 1:
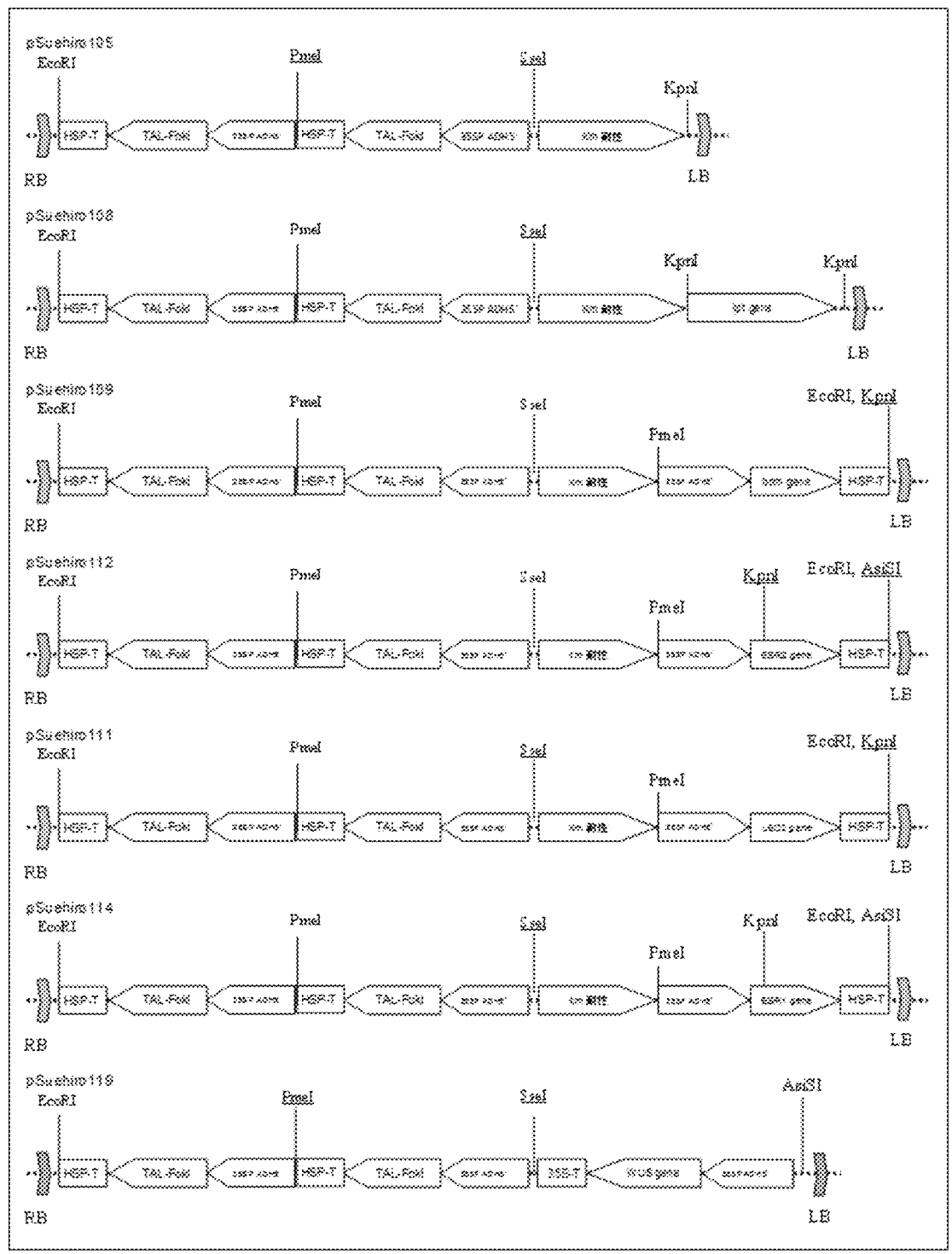
FIG. 1 is a diagram showing structures of vectors for genome editing used in transformation, and shows the right border (RB) and the left border (LB) of T-DNA of a gene portion introduced, an internal structure between these borders, and restriction enzyme sites.

In a method for producing a genome-edited plant of the present invention, a construct that expresses a gene encoding a genome editing enzyme targeting a specific gene on a genome and a gene encoding a protein that induces or promotes regeneration of a plant is first introduced into a plant cell (step (a)).

The "genome editing enzyme" in the present invention is not particularly limited as long as the "genome editing enzyme" is capable of site-specifically editing a genome, and the "genome editing enzyme" is representatively a nuclease (typically, an endonuclease) having a binding capacity to a site-specific DNA or a complex of a nuclease and an RNA. The nuclease includes, for example, fusion proteins such as ZFNs (U.S. Pat. Nos. 6,265,196, 8,524,500, 7,888,121, European Patent No. 1720995), TALENs (U.S. Pat. Nos. 8,470,973, 8,586,363), PPR (pentatricopeptide repeat) fused with a nuclease domain (Nakamura et al., Plant Cell Physiol 53: 1171-1179 (2012)). TALENs include, for example, mutants with improved activities such as platinum TALEN (Sakuma et al., Scientific Reports, 3, 3379, (2013)) and super TALEN, and any of these may be used. By designing the amino acid sequence of the DNA-binding domain (ZF, TALE, PPR) in the fusion protein such that the domain binds to the target DNA region in the specific gene on the genome, it is possible to prepare a fusion protein targeting the specific gene on the genome. The nuclease domain of the fusion protein may be substituted with a different modifying enzyme domain. The different modifying enzyme domain includes, for example, deaminase domain. Hence, the "editing" of a genome in the present invention includes not only genome alteration through cleavage by a nuclease but also genome alteration through the other modification of a genome such as deamination.

In addition, the complex of a nuclease and a guide RNA includes CRISPR-Cas9 (U.S. Pat. No. 8,697,359, International Publication No. 2013/176772), CRISPR-Cpf1 (Zetsche B. et al., Cell, 163 (3):759-71, (2015)), and the like. As Cas9 protein, SaCas9, SpCas9, and the like from various origins are publicly known (for example, U.S. Pat. Nos. 8,697,359, 8,865,406, International Publication No. 2013/176772, and the like), and any of these may be utilized. As Cpf1 protein as well, various proteins such as LbCpf1, AsCpf1, and FnCpf1 are known, and for example, those described in literatures (Zetsche, B. et al. Cell 163 (3), 759-71 (2015), Endo et al. Sci. Rep. 6, 38169 (2016)) may be utilized. Moreover, those obtained by fusing a nuclease such as Cas9 and Cpf1 with a different modifying enzyme domain such as a deaminase domain may be used. In this case, the nuclease activity of Cas9 and Cpf1 may be partially or completely abolished by introduction of a mutation, or the like.

The guide RNA contains a nucleic acid sequence (protein-binding segment) that interacts with a genome editing enzyme and thus forms a complex with the genome editing enzyme (that is, binds through non-covalent bonding interaction). In addition, the guide RNA contains a nucleic acid sequence (DNA targeting segment) complementary with a nucleic acid sequence of a target DNA region and thus gives target specificity to the complex. In this way, the genome editing enzyme is induced into the target DNA region by binding itself with the protein-binding segment of the guide RNA and can cleave the target DNA by its activity. Hence, by designing a nucleic acid sequence of the above-described guide RNA as a nucleic acid sequence complementary with a target DNA region in a specific gene on the genome, it is possible to prepare a CRISPR-Cas system targeting the specific gene on the genome.

In order to target a plurality of DNA regions, or in order to target a plurality of portions in the same DNA region, a plurality of types of guide RNAs may be used. In the case of utilizing the nCas9 protein, a plurality of types of guide RNAs each targeting one portion (two portions in total) for each chain in the double-strand of the target DNA region may be used, for example.

The "protein that induces or promotes regeneration of a plant" is not particularly limited as long as the protein can become a selection marker. Here, the "protein that induces regeneration of a plant" means a protein that can induce regeneration of a plant even under conditions where the plant is usually not regenerated (for example, in culture using a growth medium that contains no plant hormones), and the "protein that promotes regeneration of a plant" means a protein that can promote regeneration of a plant under conditions where the plant is usually regenerated (including a condition where the plant is regenerated with a low efficiency) as compared with a case where the protein is not expressed.

Such proteins include, for example, proteins involved in biosynthesis of plant hormones, transcription factors that control expression of these proteins, proteins that directly contribute to regeneration of plants, and the like. Specifically, such proteins include, for example, ipt (isopentenyl transferase/NPLs 5, 6), bbm (Baby Boom/NPLs 7 to 9), ESR1 (Enhancer of Shoot Regeneration1/NPL 10), ESR2 (Enhancer of Shoot Regeneration2/NPL 11), WUS (WUSCHEL/Zuo et al. Plant J. 30: 349-359 (2002)), STM (Shootmeristemless MERISTEMLESS/Endrizzi et al. Plant J. 10: 967-979. (1996)), iaaM (tryptophan monooxygenease) and iaaH (indoleacetamide hydrolase) (Sitbon et al. Plant Physiol 99: 1062-1069 (1992)), which are Auxin biosynthesis enzymes, Class 1 KNOX (knotted-like) homeobox (Hake et al. Annu Rev Cell Dev Biol 20: 125-151 (2004)), PLT1 (Plethoral/Aida et al. Cell 119: 109-120 (2004)), PLT2 (Plethoral/Plethoral/Aida et al. Cell 119: 109-120 (2004)), MPΔ (MONOPTEROS/AUXIN RESPONSE FACTOR5/MP/ARF5 irrepressible variant/Krogan, Berleth. Plant Signal. Behav. 7: 940-943 (2012)), LEC1 (Leafy Cotyledon)/Lotan et al. Cell 93:1195-1205 (1998)), LEC2 (Leafy Cotyledon2/Stone et al. Proc Natl Acad Sci USA 98: 11806-11811 (2001)), WUS (Wuschel/Mayer, K. F. et al. Cell 95: 805-815 (1998)), and the like. Besides these, several proteins are known (NPL 10).

The above-described genome editing enzyme and protein that induces or promotes regeneration of a plant may be homologs, analogs, or mutants of publicly-known proteins as long as they have target functions or activities. These homologs may have an amino acid sequence in which one to a plurality of amino acids are deleted, substituted, added, or inserted relative to an amino acid sequence of the target protein. Here, "plurality" is 1 to 50, preferably 1 to 3, and further preferably 1 to 10. In addition, the homologs may have a sequence identity of 80% or more, more preferably 90% or more, further preferably 95% or more, and most preferably 99% or more with the amino acid sequence of the target protein. The comparison of amino acid sequences can be made using publicly-known methods and may be conducted by, for example, BLAST (Basic Local Alignment Search Tool at the National Center for Biological Information (the Basic Local Alignment Search Tool of the National Center for Biological Information of the United States)) or the like with the default settings, for example.

In the construct that express a gene encoding a genome editing enzyme and a gene encoding a protein that induces or promotes regeneration of a plant, normally these exogenous genes bind to the downstream of an appropriate promoter that is capable of being expressed in a plant. As the promoter, a publicly-known promoter such as CaMV 35S promoter, rice actin promoter, or ubiquitin promoter may be used, for example. In addition, to the downstream of these genes, a terminator is normally bound.

As a method for introducing a construct into a plant cell, publicly-known methods such as the *Agrobacterium* method, the rubbing inoculation method, the particle gun method, and the electroporation method can be utilized, for example. In the case of utilizing the *Agrobacterium* method, as the construct, the *Agrobacterium tumefaciens* Ti plasmid of, the Ri plasmid of *Agrobacterium rhizogenes*, and vectors (for example, binary vectors) from these may be utilized, for example.

The plant cell is not particularly limited and includes cells of various plants such as vegetables, fruits, and horticultural crops. The plant includes Solanaceae plants (for example, potato, eggplant, bell pepper, tomato, chili pepper, *petunia*, tobacco), Poaceae plants (rice, barley, rye, Japanese millet, sorghum, corn), Brassicaceae plants (for example, daikon radish, turnip rape, cabbage, *Arabidopsis thaliana*, Japanese horse-radish, shepherd's-purse), Rosaceae plants (for example, Japanese apricot, peach, apple, pear, strawberries, rose), Fabaceae plants (for example, soybean, adzuki bean, common bean, green pea, broad bean, peanut, clover, burr medic), Cucurbitaceae plants (for example, sponge gourd, squash, cucumber, watermelon, melon, zucchini), Lamiaceae plants (for example, lavender, Japanese mint, Japanese basil), Liliaceae plants (for example, green onion, garlic, lily, tulip), Chenopodiaceae plants (for example, spinach), Apiaceae plants (for example, wild celery, carrot, mitsuba, celery), Asteraceae plants (for example, *chrysanthemum*, lettuce, artichoke), Orchidaceae plants (for example, moth orchids, cattleya orchids), Convolvulaceae plants (for example, sweet potato), Araceae plants (for example, *Colocasia esculenta*, taro, konjac), Rutaceae plants (for example, unshu mikan, yuzu, hassaku), Oleaceae plants (for example, olive, sweet osmanthus, jasmine, lilac), and the like, but is not limited to these.

In addition, from the viewpoint of having vegetatively propagated cultivars, the plant includes, for example, tree fruits such as potato, sweet potato, *Colocasia esculenta*, and citrus, strawberry, and the like, but is not limited to these.

In the present invention, subsequently, a plant cell obtained in step (a) is cultured and a regenerated plant is selected (step (b)).

In general, when a plant is regenerated, plant hormones such as cytokinin and auxin are added to a basal growth medium in an optimum concentration depending on the plant species, cultivar, tissue, and the like, and then used. On the other hand, there is also a case where regeneration does not occur depending on the plant species, cultivar, tissue, and the like. In the present invention, by utilizing a gene encoding a protein that induces or promotes regeneration of a plant, it is made possible to select a regenerated plant by performing culturing under a condition where a plant is normally not regenerated, and to select a regenerated plant by performing culturing under a condition where a plant is normally unlikely to be regenerated (for example, the regeneration efficiency is poor.

The "condition where plant is not regenerated" may vary depending on the plant species, cultivar, tissue cell, and the like. The culture condition where a plant is not regenerated includes, for example, culture in basal growth mediums such as the MS medium, the B5 medium, the Kano medium which do not contain plant hormones, and the tissue•cell of which is not regenerated in many plant species includes isolated protoplasts and the like.

The "condition where a plant is unlikely to be regenerated (for example, the regeneration efficiency is poor)" may vary depending on the plant species, cultivar, tissue•cell, and the like. For example, in the case of potato, it is known that May Queen has a relatively high regeneration ability and a high transformation efficiency while Toyoshiro has a low regeneration ability and a low transformation capacity (Ishige et al. Plant Sci. 73:167-174 (1991)). Hence, the tissue•cell of which a plant is unlikely to be regenerated includes, for example, the tissue•cell of Toyoshiro potato and the like.

The regeneration of a plant can be evaluated, for example, based on indices such as formation of an adventitious bud, formation of an adventitious root, and formation of an adventitious embryo.

As the approach for regeneration of a plant including the conditions on selection of a plant, a publicly-known method, for example a method described in a literature (Tabei Y. Ed., "Protocols of Transformation [Plants], Kagaku-Dojin Publishing Company, INC, 2012) can be utilized. A person skilled in the art can set appropriate conditions depending on the plant species, cultivar, tissue•cell, and the like, referring to these literatures and the like.

Note that as other aspects, it is possible to introduce a genome editing enzyme and a protein that induces or promotes regeneration of a plant into a plant cell or to introduce an RNA encoding a genome editing enzyme and an RNA encoding a protein that induces or promotes regeneration of a plant into a plant cell. In this case, however, the action is transient, so it is considered that negative selection based on an index of morphological defect such as shortened internode becomes difficult.

In the present invention, subsequently, a plant in which the gene encoding a genome editing enzyme and the gene encoding a protein that induces or promotes regeneration of a plant are not incorporated in the genome is selected from plants selected in the step (b) (step (c)).

Whether or not the gene encoding a genome editing enzyme and the gene encoding a protein that induces or promotes regeneration of a plant are incorporated in the genome may be evaluated, for example, using primers capable of amplifying these exogenous genes, performing polymerase chain reaction (PCR) on the DNA using a genomeDNA from the plant as a template, and using the presence or absence of amplicon as an index.

In addition, in the case where a plant constitutively expressed by incorporating a gene encoding a protein that induces or promotes regeneration of a plant into the genome exhibits a morphological defect, the incorporation of these exogenous genes in the genome can be evaluated simply and efficiently using the morphological defect as an index. Here, the "morphological defect" includes, for example, a shortened internode, formation of a multiple shoot, formation of a callus, and the like, although it varies depending on the type of a protein that induces or promotes regeneration of a plant. In the present invention, as a result of these evaluations, a plant in which exogenous genes are not incorporated is selected.

Note that in a selected plant, whether or not the genome is site-specifically edited can be checked by a publicly-known method. For example, the site-specific genome editing can be checked directly by amplifying a DNA region containing the target sequence of the genome editing enzyme through polymerase chain reaction (PCR), determining the nucleic acid sequence of an amplicon, and comparing the nucleic acid sequence with a sequence of a plant that is not genome-edited. Alternatively, the site-specific genome editing can be checked indirectly by a method performing electrophoresis on the amplicon and analyzing the mobility (for example, heteroduplex mobility assay), and the like.

The present invention also provides a genome-edited plant thus produced. Since the present invention utilizes a genome editing enzyme, it is possible to obtain a plant in which the genome is site-specifically edited, unlike the conventional methods that select from plants subjected to the mutagen processing. In addition, it is also possible to edit the genomes of all alleles. Moreover, it is possible to perform the genome editing of a plant without incorporating exogenous genes such as a gene encoding a genome editing enzyme into the genome, and thus there is no need for removing exogenous genes introduced into the genome by hybridization like the conventional methods. Hence, the genome-edited plant of the present invention is preferably a genome-edited plant having (a) to (c) characteristics described below.

(a) Mutation is introduced in a specific gene on a genome by a genome editing enzyme
(b) An exogenous gene is not incorporated in the genome
(c) Hybridization does not occur after the editing of the genome by the genome editing enzyme Such a genome-edited plant is advantageous in that this makes it possible to obtain a genome-edited plant while maintaining the identity of the cultivar in a plant that requires vegetative propagation to be performed from the viewpoint of cultivar maintenance and the like. From such a viewpoint, the genome-edited plant of the present invention is preferably a plant having a vegetatively propagated cultivar, and potato is particularly preferable.

The preferable form of the genome-edited plant of the present invention is one in which a mutation is introduced in a gene encoding a steroidal glycoalkaloid biosynthesis enzyme by a genome editing enzyme. The introduction of the mutation makes it possible to reduce the accumulation of steroidal glycoalkaloids in the plant (including complete elimination).

The steroidal glycoalkaloid biosynthesis enzyme is not particularly limited but includes, for example, the SSR2 gene (PTL 1, NPL 13), the PGA1 gene or PGA2 gene (NPL 14), the 16DOX gene (NPL 15), the E gene (PGA3 gene) (PTL 2), the Y gene (PGA4 gene) (PTL 3). In addition, the steroidal glycoalkaloids include, for example, solanine and chaconine.

Note that all the literatures cited in the Specification are incorporated as they are in the Specification by reference.

EXAMPLES

Hereinbelow, the present invention is described in further detail by showing Examples, but the present invention is not limited to these Examples.

(Example 1) Construction of Genome-Edited Plants Using Ipt Gene (1) Construction of Vectors Containing Ipt Gene A gene was amplified by performing PCR (30 cycles, using PrimeStar of Takara Bio Inc.) at an annealing temperature of 55° C. using primers U1126: CACCGGTACCCGTTACAAGTATTGCACGTTTTGT (SEQ ID NO: 1) and U1127: GGATCCATCGATTAAGTGATTATCGAACG (SEQ ID NO: 2) synthesized based on the sequence (ACCESSION X17432) of the ipt gene, which is registered in the DDBJ, with the DNA (U.S. Pat. No. 3,905,607) of the *Agrobacterium tumefaciens* A281 strain as a template. This gene was cloned into the pENTR/D-TOPO vector (Thermo Fisher Scientific) to obtain gene fragments.

A plant transformation vector pSuehiro108 was prepared by binding the 35S RNA promoter (35SP) of cauliflower mosaic virus, the 5' untranslated sequence (ADH5') of *Arabidopsis thaliana*, the dimer of platinum TALEN targeting the SSR2 gene of potato (two types of TAL-FokI), and the *Arabidopsis* HSP gene terminator (HSP-T) in the forward direction, and the kanamycin selection marker gene (Km resistance) and the ipt gene fragment in the opposite direction, utilizing restriction enzyme sites set in the opposite ends, based on the binary vector pKT11 (Japanese Patent Application Publication No. 2001-161373) (FIG. 1). Note that as the target sequence of SSR2, the same region as that described in a literature (Sawai et al., Plant Cell. 9, 3763-74 (2014)) was utilized. The platinum TALEN was prepared based on a literature (Sakuma et al., Scientific Reports 3, 3379 (2013)). At the same time, a vector pSuehiro105 that did not contain the ipt gene was prepared (FIG. 1). Note that pSuehiro105 was already released in the 35th meeting (Saitama) of Japanese Society for Plant Cell and Molecular Biology (meeting brief, p 118).

(2) Construction of Potato Regenerated Plants Using Ipt Gene

The vector prepared in (1) was introduced into *Agrobacterium tumefaciens* GV3101 strain by the freeze-thawing method. The *Agrobacterium tumefaciens* GV3110 strain containing the vector was shake-cultured at 28° C. for 12 hours in a YEB liquid medium [5 g/l of beef extract, 1 g/l of yeast extract, 5 g/l of peptone, 5 g/l of sucrose, 2 mM of magnesium sulfate (pH 7.2)] containing 50 ppm of kanamycin. Then, 1.5 ml of the culture liquid was subjected to centrifugal harvesting at 10,000 rpm for 3 minutes, and was then resuspended into an MS medium [Murashige & Skoog, Physiol. Plant., 15, 473-497 (1962)] containing 1.5 ml of 3% sucrose to make a bacterial culture for infection.

A stem cleaved into 3-5 mm that did not contain the node from the potato cultivar "Sassy" cultured in vitro was used as a material for infection with *Agrobacterium*. After immersed into the above-described *Agrobacterium* bacterial culture, this was placed on a sterilized paper filter to remove an excess *Agrobacterium*. This was placed on an MS medium (containing 100 μM of acetosyringone and 0.8% of agar) in a petri dish to culture for 3 days. The culture was performed at 25° C. under a condition with illumination for 16 hours (photon flux density 32 μE/m$^2$s)/without illumination for 8 hours. Subsequently, passage was made every two weeks in a growth medium containing 250 ppm of carbenicillin instead of acetosyringone.

As a result, an adventitious bud was not formed from a stem that was not treated with *Agrobacterium* and a stem that was infected with *Agrobacterium* holding the vector pSuehiro105 not containing the ipt gene. On the other hand, from the stem that was transformed with pSuehiro108 containing the ipt gene, an adventitious bud was formed. Shoots that extended from the adventitious bud were put into the same growth medium to be cultured, so that 131 rooted regenerated plants were obtained.

(3) Evaluation of Incorporation of Exogenous Gene into Genome in Regenerated Plant Using Ipt Gene and Genome Editing DNA was extracted from the regenerated plants. Whether or not the exogenous gene was incorporated in the genome of the obtained plant was determined with the kanamycin resistance gene used as the exogenous gene as an index. Specifically, PCR (30 cycles, using TakaraTaq of Takara Bio Inc.) was performed at an annealing temperature of 55° C. using primers TN5-1: CTCACCTTGCTCCTGCCGAGA (SEQ ID NO: 3) and TN5-2: CGCCTTGAGCCTGGCGAACAG (SEQ ID NO: 4) which specifically amplify the kanamycin resistance gene to detect the gene incorporated in the genome of the plant.

In addition, for evaluation on whether or not the genome was site-specifically edited in the obtained plant, a heteroduplex mobility assay (HMA) was used. PCR (35 cycles, using TakaraTaq of Takara Bio Inc.) was performed at an annealing temperature of 55° C. using primers U1131: TCACATCTTTGGATTGTTCTCTG (SEQ ID NO: 5) and U1017: TGGACCATAAATCATGCCTTC (SEQ ID NO: 6) between which the target sequence of the SSR2 gene was inserted, performing analysis using a microchip electrophoresis device "MultiNA" (Shimadzu Corporation).

Figure 2:
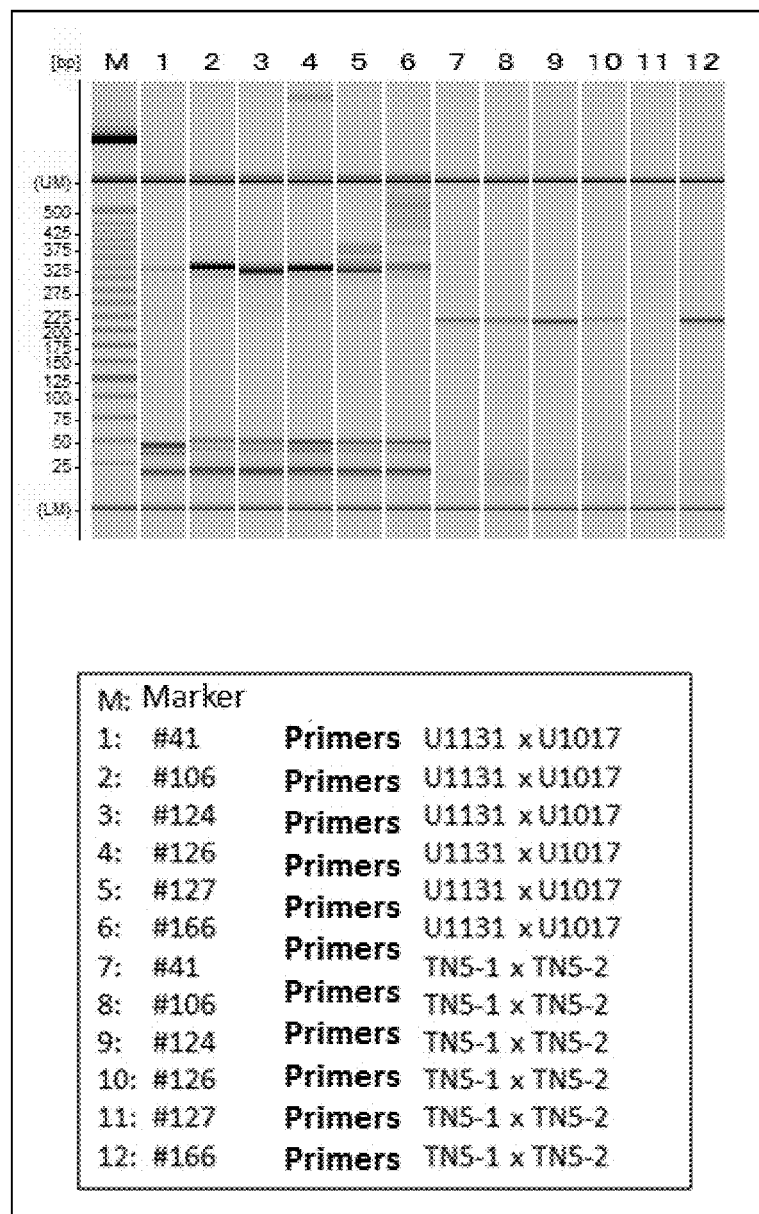
FIG. 2 is an electrophoresis image showing results of a heteroduplex mobility assay (HMA; lanes 1 to 6) that detected genome editing on potato transformed using pSuehiro108 and polymerase chain reaction (PCR; lanes 7 to 12) that determined whether or not there were transformants. In HMA, in a case where multiple bands were observed on the high molecule side, this indicates that genome editing occurred.
Figure 3:
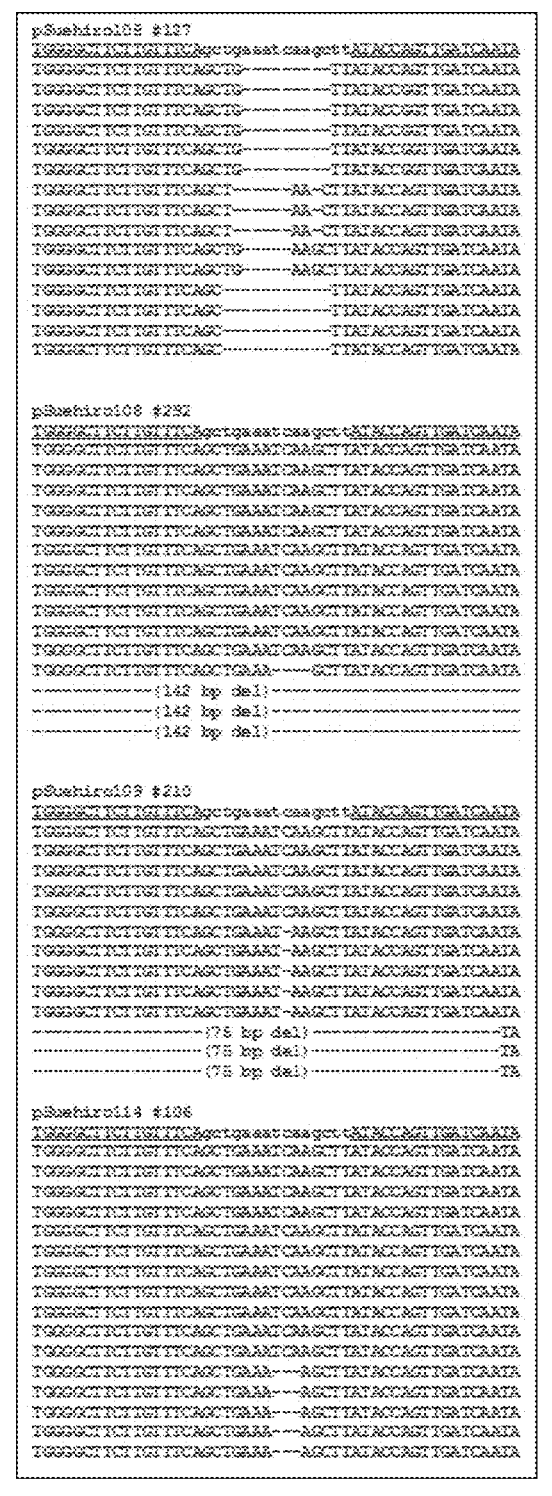

As a result, among the 131 plants regenerated from Sassy, a plant (#127) in which the exogenous gene was not incorporated in the genome but the genome was edited was obtained (FIG. 2). Besides this, one plant (#166) in which the exogenous gene was incorporated in the genome and the genome was edited and 7 plants in which the exogenous gene was incorporated in the genome but the genome was not edited (among these, #41, #106, #124, #126 are shown in FIG. 2) were obtained. In the plants in which the exogenous gene was incorporated in the genome, the internode was narrowed and a morphological defect (teratoma symptom) such as multiple shoot was observed, so that it was confirmed the ipt gene functioned as a negative selection marker. An amplified fragment DNA near the target sequence of platinum TALEN in the genome of #127 plant was cloned into TOPO® TA Cloning® Kit for Sequencing (Thermo Fisher Scientific) to obtain gene fragments. Then, 15 nucleic acid sequences cloned into *Escherichia coli* were determined. It was confirmed that genome editing including deletion occurred in each sequence and that there was no non-damaged sequence and complete deletion occurred (FIG. 3). As to the deletion, 5, 7, 9, and 11 bases were observed and any normal sequence was not observed. 5, 7, and 11 bases where frames are shifted make it impossible to express a normal SSR2 protein. Since this region is important for the activity, deletion of the 9 base also makes it impossible to produce an SSR2 protein having activity. For this reason, it was found that #127, which did not have a normal SSR2 gene sequence exhibited a phenotype in which the content of steroidal glycoalkaloid was very low. It was found that potato that had a very low content of steroidal glycoalkaloid and contains no transgene was obtained using the present method.

When the same experiment was repeated, a plant (#292) in which the exogenous gene was not incorporated in the genome but the genome was edited was identified from regenerated 93 plants. Besides this, 4 plants (#234, #247, #251, and #290) in which the exogenous gene was incorporated in the genome and the genome was edited were identified, and 28 plants which were transformed and in which the genome was not edited were obtained. An amplified fragment of #292 plant was amplified by PCR (35 cycles, using TakaraExTaq of Takara Bio Inc.) at an annealing temperature of 55° C. using primers U1131: TCACATCTTTGGATTGTTCTCTG (SEQ ID NO: 5) and U1017: TGGACCATAAATCATGCCTTC (SEQ ID NO: 6) between which the target sequence of the SSR2 gene was inserted, and was cloned into the pCR4 TOPO Vector vector (Thermo Fisher Scientific) to obtain gene fragments. Then, 15 nucleic acid sequences cloned into *Escherichia coli* were determined. Here, genome editing including deletion occurred in 4 sequences but 11 sequences were not damaged. Thus, it was confirmed that incomplete deletion occurred (FIG. 3).

Similarly, 181 regenerated plants and 117 regenerated plants were obtained from potato cultivars "Sayaka" and "May Queen". Among the regenerated plants from Sayaka, plants (#91, 112, 117, 164) in which the exogenous gene was not incorporated in the genome but the genome was edited were obtained. Besides these, 9 plants in which the exogenous gene was incorporated in the genome and the genome was edited and 4 plants in which the exogenous gene was incorporated in the genome but the genome was not edited were obtained. Amplified fragment DNAs near the target sequence of platinum TALEN in the genome of #112 plant and #117 plant, which were expected to have large deletion in the heteroduplex mobility assay, were cloned into TOPO® TA Cloning® Kit for Sequencing (Thermo Fisher Scientific) to obtain gene fragments. Then, 15 nucleic acid sequences cloned into *Escherichia coli* were determined. It was confirmed that genome editing including deletion occurred in each sequence and that there was no non-damaged sequence and complete deletion occurred (FIG. 4). By similarly confirming the regenerated plants from May Queen, it is possible to obtain plants which were not transformed but in which the genome was edited.

(Example 2) Construction of Genome-Edited Plants Using Bbm Gene (1) Construction of Vectors Containing Bbm Gene A gene was amplified by performing PCR (30 cycles, using PrimeStar of Takara Bio Inc.) at an annealing temperature of 55° C. using primers U1145: CACCTCTAGAATGAATCAAACCCAACGTTGG (SEQ ID NO: 7) and U1146: CTAAGTGTCGTTCCAAACTGAAAAC (SEQ ID NO: 8) synthesized based on the sequence (ACCESSION NM_001343497) of the bbm gene, which is registered in the DDBJ, with the cDNA synthesized from all the RNA extracted from the premature seed of *Arabidopsis thaliana* (ecotype Columbia) (provided by Riken, Keiko Sakakibara senior research scientist) as a template. This gene was cloned into the pENTR/D-TOPO vector (Thermo Fisher Scientific) to obtain gene fragments. A plant transformation vector pSuehiro109 was prepared by binding the 35S RNA promoter of the cauliflower mosaic virus, the 5' untranslated sequence of *Arabidopsis thaliana*, the bbm gene, and the *Arabidopsis* HSP gene terminator, utilizing restriction enzyme sites set in the opposite ends, based on the binary vector pSuehiro105 (FIG. 1).

(2) Construction of Potato Regenerated Plants Using Bbm Gene

The vector prepared in (1) was introduced into *Agrobacterium tumefaciens* GV3101 strain by the freeze-thawing method. The *Agrobacterium tumefaciens* GV3110 strain containing the vector was shake-cultured at 28° C. for 12 hours in a YEB liquid medium [5 g/l of beef extract, 1 g/l of yeast extract, 5 g/l of peptone, 5 g/l of sucrose, 2 mM of magnesium sulfate (pH 7.2)] containing 50 ppm of kanamycin. Then, 1.5 ml of the culture liquid was subjected to centrifugal harvesting at 10,000 rpm for 3 minutes, and was then resuspended into an MS medium [Murashige & Skoog, Physiol. Plant., 15, 473-497 (1962)] containing 1.5 ml of 3% sucrose to make a bacterial culture for infection.

A stem cleaved into 3-5 mm that did not contain the node from the potato cultivar "Sassy" cultured in vitro was used as a material for infection with *Agrobacterium*. After immersed into the above-described *Agrobacterium* bacterial culture, this was placed on a sterilized paper filter to remove an excess *Agrobacterium*. This was placed on an MS medium (containing 100 μM of acetosyringone and 0.8% of agar) in a petri dish to culture for 3 days. The culture was performed at 25° C. under a condition with illumination for 16 hours (photon flux density 32 μE/m$^2$s)/without illumination for 8 hours. Subsequently, passage was made every two weeks in a growth medium containing 250 ppm of carbenicillin instead of acetosyringone. An adventitious bud was not formed from a stem that was not treated with *Agrobacterium* and a stem that was infected with the vector not containing the bbm gene. On the other hand, from the stem that was transformed with pSuehiro109 containing the bbm gene, an adventitious bud was formed. 126 shoots that extended from the adventitious bud were put into the same growth medium to be cultured. Similarly, 198 regenerated plants were obtained from the potato cultivar "Sayaka". Also, 89 shoots that extended from the adventitious bud were put into the same growth medium to be cultured. Similarly, 194 regenerated plants and 134 regenerated plants were obtained from the potato cultivars "Sayaka" and "May Queen".

(3) Evaluation of Incorporation of Exogenous Gene into Genome in Regenerated Plant Using Ipt Gene and Genome Editing DNA was extracted from the regenerated plants. Whether or not the exogenous gene was incorporated in the genome of the obtained plant was determined with the kanamycin resistance gene used as the exogenous gene as an index. Specifically, PCR (30 cycles, using TakaraTaq of Takara Bio Inc.) was performed at an annealing temperature of 55° C. using primers TN5-1: CTCACCTTGCTCCTGCCGAGA (SEQ ID NO: 3) and TN5-2: CGCCTT-GAGCCTGGCGAACAG (SEQ ID NO: 4) which specifically amplify the kanamycin resistance gene to detect the gene incorporated in the genome of the plant.

In addition, for evaluation on whether or not the genome was site-specifically edited in the obtained plant, a heteroduplex mobility assay (HMA) was used. PCR (35 cycles, using TakaraTaq of Takara Bio Inc.) was performed at an annealing temperature of 55° C. using primers U1131: TCACATCTTTGGATTGTTCTCTG (SEQ ID NO: 5) and U1017: TGGACCATAAATCATGCCTTC (SEQ ID NO: 6) between which the target sequence of the SSR2 gene was inserted, performing analysis using a microchip electrophoresis device "MultiNA" (Shimadzu Corporation). As a result, among 95 plants regenerated from Sassy and tested as samples, a plant (#210) which was not transformed but in which the genome was edited was obtained (FIG. 3). Besides this, no plant which was transformed and in which the genome was edited was obtained. In addition, 6 plants which were transformed but in which the genome was not edited were obtained. An amplified fragment of #210 plant was amplified by performing PCR (35 cycles, using Takara-ExTaq of Takara Bio Inc.) at an annealing temperature of 55° C. using primers U1131: TCACATCTTTGGAT-TGTTCTCTG (SEQ ID NO: 5) and U1017: TGGACCAT-AAATCATGCCTTC (SEQ ID NO: 6) between which the target sequence of the SSR2 gene was inserted, to be cloned into the pCR4 TOPO Vector vector (Thermo Fisher Scientific) to obtain gene fragments. Then, 13 nucleic acid sequences cloned into *Escherichia coli* were determined. Although genome editing including deletion occurred in 3 sequences, 10 sequences were not damaged at all. It was thus confirmed that incomplete deletion occurred (FIG. 3). Confirmation was made similarly for the regenerated plants from Sayaka and May Queen and plants which were not transformed but in which the genome was edited were obtained.

(Example 3) Construction of Genome-Edited Plants Using ESR2 Gene (1) Regeneration Promotion and Construction of Vectors Containing ESR2 Gene, which is Negative Selection Marker Gene of Transformant Since the ESR2 gene has no intron for all the genomes extracted from the plant of *Arabidopsis thaliana* (ecotype Columbia), a gene was amplified by performing PCR (30 cycles, using PrimeStar of Takara Bio Inc.) at an annealing temperature of 55° C. using primers U1157: CACCTCTAGAATGGAAGAAGCAATCATGAGACT (SEQ ID NO: 9) and U1158: CTAATAATCATCAT-GAAAGCAATACTGA (SEQ ID NO: 10) synthesized based on the sequence (ACCESSION NM_102301) registered in the DDBJ. This was cloned into the pENTR/D-TOPO vector (Thermo Fisher Scientific) to obtain gene fragments. A plant transformation vector pSuehiro112 was prepared by binding the 35S RNA promoter of the cauliflower mosaic virus, the 5' untranslated sequence of *Arabidopsis thaliana*, the gene, and the *Arabidopsis* HSP gene terminator, utilizing restriction enzymes set in the opposite ends, based on the binary vector pSuehiro105 (FIG. 1).

(2) Construction of Potato Regenerated Plants Using ESR2 Gene

The vector prepared in (1) was introduced into *Agrobacterium tumefaciens* GV3101 strain by the freeze-thawing method. The *Agrobacterium tumefaciens* GV3110 strain containing the vector was shake-cultured at 28° C. for 12 hours in the YEB liquid medium [5 g/l of beef extract, 1 g/l of yeast extract, 5 g/l of peptone, 5 g/l of sucrose, 2 mM of magnesium sulfate (pH 7.2)] containing 50 ppm of kanamycin. Then, 1.5 ml of a culture liquid was subjected to centrifugal harvesting at 10,000 rpm for 3 minutes, and was then resuspended into an MS medium [Murashige & Skoog, Physiol. Plant., 15, 473-497 (1962)] containing 1.5 ml of 3% sucrose to make a bacterial culture for infection.

A stem cleaved into 3-5 mm that did not contain the node from the potato cultivar "Sassy" cultured in vitro was used as a material for infection with *Agrobacterium*. After immersed into the above-described *Agrobacterium* bacterial culture, this was placed on a sterilized paper filter to remove an excess *Agrobacterium*. This was placed on an MS medium (containing 100 μM of acetosyringone and 0.8% of agar) in a petri dish. The culture was performed for 3 days at 25° C. under a condition with illumination for 16 hours (photon flux density 32 $\mu E/m^2 s$)/without illumination for 8 hours. Subsequently, passage was made every two weeks in a growth medium containing 250 ppm of carbenicillin instead of acetosyringone. An adventitious bud was not formed from a stem that was not treated with *Agrobacterium* and a stem that was infected with the vector not containing the ESR2 gene. On the other hand, from the stem that was transformed with pSuehiro112 containing the ESR2 gene, an adventitious bud was formed. Shoots that extended from the adventitious bud were put into the same growth medium to be cultured, so that 88 rooted regenerated plants were obtained.

(3) Evaluation of Transformant of Regenerated Plant Using ESR2 Gene and Genome Editing DNA was extracted from the regenerated plants. The evaluation of each transformant is conducted by performing PCR (30 cycles, using TakaraTaq of Takara Bio Inc.) at an annealing temperature of 55° C. using primers TN5-1: CTCACCTTGCTCCTGCCGAGA (SEQ ID NO: 3) and TN5-2: CGCCTTGAGCCTGGCGAACAG (SEQ ID NO: 4) which specifically amplify the sequence of the kanamycin resistance gene to detect the plant containing the kanamycin resistance gene as an exogenous gene, making it possible to confirm whether or not the regenerated plant is a transformant plant. The evaluation of each genome-edited plant was conducted using a heteroduplex mobility assay (HMA). PCR (35 cycles, using TakaraTaq of Takara Bio Inc.) was performed at an annealing temperature of 55° C. using primers U1131: TCACATCTTTGGATTGTTCTCTG (SEQ ID NO: 5) and U1017: TGGACCATAAATCATGCCTTC (SEQ ID NO: 6) between which the target sequence of the SSR2 gene was inserted, performing analysis using a microchip electrophoresis device MultiNA (Shimadzu Corporation). plants which are not transformed but in which the genome was edited can be obtained by checking plants regenerated and tested as samples. In addition, it is possible to obtain potato whose cultivar's character is maintained, in which a mutation has occurred in all allele but a mutation has not occurred in the other genes, and which has a very low steroidal glycoalkaloid.

(Example 4) Construction of Genome-Edited Plants Using LEC2 Gene (1) Regeneration Promotion and Construction of Vectors Containing LEC2 Gene which is Negative Selection Marker Gene of Transformant On a cDNA synthesized from all the RNAs extracted from the premature seed of *Arabidopsis thaliana* (ecotype Columbia), PCR (30 cycles, using PrimeStar of Takara Bio Inc.) was performed at an annealing temperature of 55° C. using primers U1155: CCACTCTAGAATGGATAACTTCT-TACCCTTTCCCT (SEQ ID NO: 11) and U1156: TCAC-CACCACTCAAAGTCGTTAAA (SEQ ID NO: 12) synthesized based on the sequence (ACCESSION NM_102595), which is registered in the DDBJ, to amplify the gene. This gene was cloned into the pENTR/D-TOPO vector (Thermo Fisher Scientific) to obtain gene fragments. A plant transformation vector pSuehiro111 was prepared by binding the 35S RNA promoter of the cauliflower mosaic virus, 5' untranslated sequence of *Arabidopsis thaliana*, the gene, and the *Arabidopsis* HSP gene terminator, utilizing restriction enzyme sites set in the opposite ends, based on the binary vector pSuehiro105 (FIG. 1).

(2) Construction of Potato Regenerated Plants Using LEC2 Gene

The vector prepared in (1) was introduced into *Agrobacterium tumefaciens* GV3101 strain by the freeze-thawing method. The *Agrobacterium tumefaciens* GV3110 strain containing the vector was shake-cultured at 28° C. for 12 hours in a YEB liquid medium [5 g/l of beef extract, 1 g/l of yeast extract, 5 g/l of peptone, 5 g/l of sucrose, 2 mM of magnesium sulfate (pH 7.2)] containing 50 ppm of kanamycin. Then, 1.5 ml of a culture liquid was subjected to centrifugal harvesting at 10,000 rpm for 3 minutes, and was then resuspended into an MS medium [Murashige & Skoog, Physiol. Plant., 15, 473-497 (1962)] containing 1.5 ml of 3% sucrose to make a bacterial culture for infection.

A stem cleaved into 3-5 mm that did not contain the node from the potato cultivar "Sassy" cultured in vitro was used as a material for infection with *Agrobacterium*. After immersed into the above-described *Agrobacterium* bacterial culture, this was placed on a sterilized paper filter to remove an excess *Agrobacterium*. This was placed on an MS medium (containing 100 µM of acetosyringone and 0.8% of agar) in a petri dish. The culture was performed for 3 days at 25° C. under a condition with illumination for 16 hours (photon flux density 32 µE/m²s)/without illumination for 8 hours. Subsequently, passage was made every two weeks in a growth medium containing 250 ppm of carbenicillin instead of acetosyringone. An adventitious bud was not formed from a stem that was not treated with *Agrobacterium* and a stem that was infected with the vector not containing the LEC2 gene. On the other hand, from a stem that was transformed with pSuehiro111 containing the LEC2 gene, an adventitious bud was formed. Shoots that extended from the adventitious bud were put into the same growth medium to be cultured, so that 91 rooted regenerated plants were obtained.

(3) Evaluation of Transformant of Regenerated Plant Using LEC2 Gene and Genome Editing DNA was extracted from the regenerated plants. The evaluation of each transformant is conducted by performing PCR (30 cycles, using TakaraTaq of Takara Bio Inc.) at an annealing temperature of 55° C. using primers TN5-1: CTCACCTTGCTCCTGCCGAGA (SEQ ID NO: 3) and TN5-2: CGCCTTGAGCCTGGCGAACAG (SEQ ID NO: 4) which specifically amplify the sequence of the kanamycin resistance gene to detect the plant containing the kanamycin resistance gene as an exogenous gene, making it possible to confirm whether or not the regenerated plant is a transformant plant. The evaluation of each genome-edited plant was conducted using a heteroduplex mobility assay (HMA). PCR (35 cycles, using TakaraTaq of Takara Bio Inc.) is performed at an annealing temperature of 55° C. using primers U1131: TCACATCTTTGGATTGTTCTCTG (SEQ ID NO: 5) and U1017: TGGACCATAAATCATGCCTTC (SEQ ID NO: 6) between which the target sequence of the SSR2 gene was inserted, making it possible to perform analysis using a microchip electrophoresis device MultiNA (Shimadzu Corporation). plants which are not transformed but in which the genome was edited can be obtained by checking plants regenerated and tested as samples. In addition, it is possible to obtain potato whose cultivar's character is maintained, in which a mutation has occurred in all allele but a mutation has not occurred in the other genes, and which has a very low steroidal glycoalkaloid.

(Example 5) Construction of Genome-Edited Plants Using ESR1 Gene (1) Regeneration Promotion and Construction of Vectors Containing ESR1 Gene which is Negative Selection Marker Gene of Transformant Since the ESR1 gene has no intron for all the genomes extracted from the plant of *Arabidopsis thaliana* (ecotype Columbia), a gene was amplified by performing PCR (30 cycles, using PrimeStar of Takara Bio Inc.) at an annealing temperature of 55° C. using primers U1163: CACCTCTAGAATGGAAAAAGCCTTGAGAAACTT (SEQ ID NO: 13) and U1164: CTATCCCCAC-GATCTTCGG (SEQ ID NO: 14) synthesized based on the sequence (ACCESSION NM 101169) registered in the DDBJ. This was cloned into the pENTR/D-TOPO vector (Thermo Fisher Scientific) to obtain gene fragments. A plant transformation vector pSuehiro114 was prepared by binding the 35S RNA promoter of the cauliflower mosaic virus, the 5' untranslated sequence of *Arabidopsis thaliana*, the gene, and the *Arabidopsis* HSP gene terminator, utilizing restriction enzyme sites set in the opposite ends, based on the binary vector pSuehiro105 (FIG. 1).

(2) Construction of Potato Regenerated Plants Using ESR1 Gene

The vector prepared in (1) was introduced into *Agrobacterium tumefaciens* GV3101 strain by the freeze-thawing method. The *Agrobacterium tumefaciens* GV3110 strain containing the vector was shake-cultured at 28° C. for 12 hours in the YEB liquid medium [5 g/l of beef extract, 1 g/l of yeast extract, 5 g/l of peptone, 5 g/l of sucrose, 2 mM of magnesium sulfate (pH 7.2)] containing 50 ppm of kanamycin. Then, 1.5 ml of a culture liquid was subjected to centrifugal harvesting at 10,000 rpm for 3 minutes, and was then resuspended into an MS medium [Murashige & Skoog, Physiol. Plant., 15, 473-497 (1962)] containing 1.5 ml of 3% sucrose to make a bacterial culture for infection.

A stem cleaved into 3-5 mm that did not contain the node from the potato cultivar "Sassy" cultured in vitro was used as a material for infection with *Agrobacterium*. After immersed into the above-described *Agrobacterium* bacterial culture, this was placed on a sterilized paper filter to remove an excess *Agrobacterium*. This was placed on an MS medium (containing 100 µM of acetosyringone and 0.8% of agar) in a petri dish. The culture was performed for 3 days at 25° C. under a condition with illumination for 16 hours (photon flux density 32 μE/m²s)/without illumination for 8 hours. Subsequently, passage was made every two weeks in a growth medium containing 250 ppm of carbenicillin instead of acetosyringone. An adventitious bud was not formed from a stem that was not treated with *Agrobacterium* and a stem that was infected with the vector not containing the ESR1 gene. On the other hand, from a stem that was transformed with pSuehiro114 containing the ESR1 gene, an adventitious bud was formed. Shoots that extended from the adventitious bud were put into the same growth medium to be cultured, so that 79 rooted regenerated plants were obtained. Similarly, 99 regenerated plants were obtained from the potato cultivar "May Queen".

(3) Evaluation of Transformant of Regenerated Plant Using ESR1 Gene and Genome Editing DNA was extracted from the regenerated plants. Whether or not the exogenous gene was incorporated in the genome of the obtained plant was determined with the kanamycin resistance gene used as the exogenous gene as an index. Specifically, PCR (30 cycles, using TakaraTaq of Takara Bio Inc.) was performed at an annealing temperature of 55° C. using primers TN5-1: CTCACCTTGCTCCTGCCGAGA (SEQ ID NO: 3) and TN5-2: CGCCTTGAGCCTGGCGAACAG (SEQ ID NO: 4) which specifically amplify the kanamycin resistance gene to detect the gene incorporated in the genome of the plant.

In addition, for evaluation on whether or not the genome was site-specifically edited in the obtained plant, a heteroduplex mobility assay (HMA) was used. PCR (35 cycles, using TakaraTaq of Takara Bio Inc.) was performed at an annealing temperature of 55° C. using primers U1131: TCACATCTTTGGATTGTTCTCTG (SEQ ID NO: 5) and U1017: TGGACCATAAATCATGCCTTC (SEQ ID NO: 6) between which the target sequence of the SSR2 gene was inserted, performing analysis using a microchip electrophoresis device "MultiNA" (Shimadzu Corporation). As a result, among 79 plants regenerated and tested as samples, a plant (#106) which was not transformed but in which the genome was edited was obtained (FIG. 3). Besides this, 5 plants (#4, #5, #19, #23, and #52) which were transformed and in which the genome was edited were obtained. In addition, 6 plants which were transformed but in which the genome was not edited were obtained. An amplified fragment of #106 plant was amplified by performing PCR (35 cycles, using TakaraExTaq of Takara Bio Inc.) at an annealing temperature of 55° C. using primers U1131: TCACATCTTTGGATTGTTCTCTG (SEQ ID NO: 5) and U1017: TGGACCATAAATCATGCCTTC (SEQ ID NO: 6) between which the target sequence of the SSR2 gene was inserted, to be cloned into the pCR4 TOPO Vector vector (Thermo Fisher Scientific) to obtain gene fragments. Then, 16 nucleic acid sequences cloned into *Escherichia coli* were determined. Although genome editing including deletion occurred in 5 sequences, 11 sequences were not damaged at all. It was thus confirmed that incomplete deletion occurred (FIG. 3).

Among the regenerated plants from May Queen, a plant (#15) in which the exogenous gene was not incorporated in the genome but the genome was edited was obtained. An amplified fragment DNA near the target sequence of platinum TALEN in the genome of #15 plant was cloned into TOPO® TA Cloning® Kit for Sequencing (Thermo Fisher Scientific) to obtain gene fragments. Then, 13 nucleic acid sequences cloned into *Escherichia coli* were determined. It was confirmed that genome editing including deletion occurred in each sequence and there was no non-damaged sequence and complete deletion occurred (FIG. 5).

(Example 6) Construction of Genome-Edited Plants Using WUS Gene (1) Regeneration Promotion and Construction of Vectors Containing WUS Gene, which is Negative Selection Marker Gene of Transformant On a cDNA synthesized from all the RNAs extracted from the flower stalk of *Arabidopsis thaliana* (ecotype Columbia), PCR (30 cycles, using PrimeStar of Takara Bio Inc.) was performed at an annealing temperature of 55° C. using primers U1187: CACCACTAGTATGGAGCCGCCACAG-CATCA (SEQ ID NO: 15) and U1188: AGATCTAGTTCA-GACGTAGCTCAAGAGAAG (SEQ ID NO: 16) synthesized based on the sequence (ACCESSION NM_127349) of the WUS gene, which is registered in the DDBJ, to amplify the gene. This gene was cloned into the pENTR/D-TOPO vector (Thermo Fisher Scientific) to obtain gene fragments. A plant transformation vector pSuehiro119 was prepared by binding the 35S RNA promoter of the cauliflower mosaic virus, the 5' untranslated sequence of *Arabidopsis thaliana*, the gene, and the 35S RNA terminator of cauliflower mosaic virus, utilizing restriction enzyme sites set in the opposite ends, based on the binary vector pSuehiro105 (FIG. 1).

(2) Construction of Potato Regenerated Plants Using WUS Gene

The vector prepared in (1) was introduced into *Agrobacterium tumefaciens* GV3101 strain by the freeze-thawing method. The *Agrobacterium tumefaciens* GV3110 strain containing the vector was shake-cultured at 28° C. for 12 hours in the YEB liquid medium [5 g/l of beef extract, 1 g/l of yeast extract, 5 g/l of peptone, 5 g/l of sucrose, 2 mM of magnesium sulfate (pH 7.2)] containing 50 ppm of kanamycin. Then, 1.5 ml of a culture liquid was subjected to centrifugal harvesting at 10,000 rpm for 3 minutes, and was then resuspended into an MS medium [Murashige & Skoog, Physiol. Plant., 15, 473-497 (1962)] containing 1.5 ml of 3% sucrose to make a bacterial culture for infection.

A stem cleaved into 3-5 mm that did not contain the node from the potato cultivar "Sayaka" cultured in vitro was used as a material for infection with *Agrobacterium*. After immersed into the above-described *Agrobacterium* bacterial culture, this was placed on a sterilized paper filter to remove an excess *Agrobacterium*. This was placed on an MS medium (containing 100 μM of acetosyringone and 0.8% of agar) in a petri dish. The culture was performed for 3 days at 25° C. under a condition with illumination for 16 hours (photon flux density 32 μE/m²s)/without illumination for 8 hours. Subsequently, passage was made every two weeks in a growth medium containing 250 ppm of carbenicillin instead of acetosyringone. An adventitious bud was not formed from a stem that was not treated with *Agrobacterium* and a stem that was infected with the vector not containing the 2WUS gene. On the other hand, from a stem that was transformed with pSuehiro119 containing the WUS gene, an adventitious bud was formed. Shoots that extended from the adventitious bud were put into the same growth medium to be cultured, so that 57 rooted regenerated plants were obtained.

(3) Evaluation of Transformant of Regenerated Plant Using WUS Gene and Genome Editing DNA was extracted from the regenerated plants. The evaluation of each transformant is conducted by performing PCR (30 cycles, using TakaraTaq of Takara Bio Inc.) at an annealing temperature of 55° C. using primers TN5-1: CTCACCTTGCTCCTGCCGAGA (SEQ ID NO: 3) and TN5-2: CGCCTTGAGCCTGGCGAACAG (SEQ ID NO: 4) which specifically amplify the sequence of the kanamycin resistance gene to detect the plant containing the kanamycin resistance gene as an exogenous gene, making it possible to confirm whether or not the regenerated plant is a transformant plant. The evaluation of each genome-edited plant was conducted using a heteroduplex mobility assay (HMA). PCR (35 cycles, using TakaraTaq of Takara Bio Inc.) is performed at an annealing temperature of 55° C. using primers U1131: TCACATCTTTGGATTGTTCTCTG (SEQ ID NO: 5) and U1017: TGGACCATAAATCATGCCTTC (SEQ ID NO: 6) between which the target sequence of the SSR2 gene is inserted, making it possible to perform analysis using a microchip electrophoresis device MultiNA (Shimadzu Corporation). plants which are not transformed but in which the genome was edited can be obtained by checking the plants regenerated and tested as samples. In addition, it is possible to obtain potato whose cultivar's character is maintained, in which a mutation has occurred in all allele but a mutation has not occurred in the other genes, and which has a very low steroidal glycoalkaloid.

INDUSTRIAL APPLICABILITY

The present invention makes it possible to perform genome editing on a plant without incorporating an exogenous gene such as a gene encoding a genome editing enzyme into the genome. Although the present invention can be applied widely in the field of agriculture, the present invention is particularly useful for genome editing of plant cultivation cultivars that require vegetative propagation from the viewpoint of cultivar maintenance and the like.

[Sequence Listing Free Text]
SEQ ID NOs: 1 to 16
<223> artificially synthesized primer sequence
[Sequence Listing]

---

The invention claimed is:

1. A method for producing a genome-edited plant in which a mutation is introduced into a specificgene on a genome and no exogenousgene is incorporated on the genome, comprising the steps of:
   (a) introducing a construct that expresses a first gene encoding a genome editing enzyme targeting the specificgene on the genome and a second gene encoding a protein that induces or promotes regeneration of a plant into at least one plant cell, wherein said second gene is an isopentenyl transferase (ipt) gene;
   (b) culturing the at least one plant cell obtained in the step (a); and
   (c) selecting a regenerated plant exhibiting transient expression of said second gene, such that in said selected plant, said first and second genes are transiently expressed and are not incorporated into the genome, wherein the selected regenerated plant is the genome-edited plant.

2. The method according to claim 1, wherein the introduction of the construct into a plant cell in the step (a) is conducting by an agrobacterium method.

3. The method according to claim 1, wherein the culturing of the plant cell in the step (b) is conducted in a growth medium that contains no plant hormones.

4. The method according to claim 1, wherein a plant in which no morphological defect has occurred is selected.

* * * * *

SEQUENCE LISTING

<160> NUMBER OF SEQ ID NOS: 30

<210> SEQ ID NO 1
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 1
caccggtacc cgttacaagt attgcacgtt ttgt                              34

<210> SEQ ID NO 2
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 2
ggatccatcg attaagtgat tatcgaacg                                    29

<210> SEQ ID NO 3
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 3
ctcaccttgc tcctgccgag a                                            21

<210> SEQ ID NO 4
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 4
cgccttgagc ctggcgaaca g                                            21

<210> SEQ ID NO 5
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 5
tcacatcttt ggattgttct ctg                                    23

<210> SEQ ID NO 6
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 6
tggaccataa atcatgcctt c                                      21

<210> SEQ ID NO 7
<211> LENGTH: 31
<212> TYPE: DNA
<213> ORGANISM: Artificial Sequence
<220> FEATURE:
<223> OTHER INFORMATION: Artificially synthesized primer sequence

<400> SEQUENCE: 7
cacctctaga atgaatcaaa cccaacgttg g                           31

<210> SEQ ID NO 8
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 8
ctaagtgtcg ttccaaactg aaaac                                  25

<210> SEQ ID NO 9
<211> LENGTH: 33
<212> TYPE: DNA
<213> ORGANISM: Artificial Sequence
<220> FEATURE:
<223> OTHER INFORMATION: Artificially synthesized primer sequence

<400> SEQUENCE: 9
cacctctaga atggaagaag caatcatgag act                         33

<210> SEQ ID NO 10
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 10
ctaataatca tcatgaaagc aatactga                               28

<210> SEQ ID NO 11
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 11
ccactctaga atggataact tcttacccct tccct                       35

<210> SEQ ID NO 12

```
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 12
tcaccaccac tcaaagtcgt taaa                                          24

<210> SEQ ID NO 13
<211> LENGTH: 33
<212> TYPE: DNA
<213> ORGANISM: Artificial Sequence
<220> FEATURE:
<223> OTHER INFORMATION: Artificially synthesized primer sequence

<400> SEQUENCE: 13
cacctctaga atggaaaaag ccttgagaaa ctt                                33

<210> SEQ ID NO 14
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 14
ctatccccac gatcttcgg                                                19

<210> SEQ ID NO 15
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 15
caccactagt atggagccgc cacagcatca                                    30

<210> SEQ ID NO 16
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 16
agatctagtt cagacgtagc tcaagagaag                                    30

<210> SEQ ID NO 17
<211> LENGTH: 49
<212> TYPE: DNA
<213> ORGANISM: Artificial Sequence
<220> FEATURE:
<223> OTHER INFORMATION: Synthetic sequence

<400> SEQUENCE: 17
tggggcttct tgtttcagct gaaatcaagc ttataccagt tgatcaata              49

<210> SEQ ID NO 18
<211> LENGTH: 40
<212> TYPE: DNA
<213> ORGANISM: Artificial Sequence
<220> FEATURE:
<223> OTHER INFORMATION: Synthetic sequence
```

<400> SEQUENCE: 18
tggggcttct tgtttcagct gttataccag ttgatcaata        40

<210> SEQ ID NO 19
<211> LENGTH: 42
<212> TYPE: DNA
<213> ORGANISM: Artificial Sequence
<220> FEATURE:
<223> OTHER INFORMATION: Synthetic sequence

<400> SEQUENCE: 19
tggggcttct tgtttcagct aacttatacc agttgatcaa ta        42

<210> SEQ ID NO 20
<211> LENGTH: 44
<212> TYPE: DNA
<213> ORGANISM: Artificial Sequence
<220> FEATURE:
<223> OTHER INFORMATION: Synthetic sequence

<400> SEQUENCE: 20
tggggcttct tgtttcagct gaagcttata ccagttgatc aata        44

<210> SEQ ID NO 21
<211> LENGTH: 38
<212> TYPE: DNA
<213> ORGANISM: Artificial Sequence
<220> FEATURE:
<223> OTHER INFORMATION: Synthetic sequence

<400> SEQUENCE: 21
tggggcttct tgtttcagct tataccagtt gatcaata        38

<210> SEQ ID NO 22
<211> LENGTH: 45
<212> TYPE: DNA
<213> ORGANISM: Artificial Sequence
<220> FEATURE:
<223> OTHER INFORMATION: Synthetic sequence

<400> SEQUENCE: 22
tggggcttct tgtttcagct gaaagcttat accagttgat caata        45

<210> SEQ ID NO 23
<211> LENGTH: 48
<212> TYPE: DNA
<213> ORGANISM: Artificial Sequence
<220> FEATURE:
<223> OTHER INFORMATION: Synthetic sequence

<400> SEQUENCE: 23
tggggcttct tgtttcagct gaaataagct tataccagtt gatcaata        48

<210> SEQ ID NO 24
<211> LENGTH: 46
<212> TYPE: DNA
<213> ORGANISM: Artificial Sequence
<220> FEATURE:
<223> OTHER INFORMATION: Synthetic sequence

<400> SEQUENCE: 24
tggggcttct tgtttcagct gaaaagctta taccagttga tcaata        46

<210> SEQ ID NO 25

```
<210> SEQ ID NO 25
<211> LENGTH: 47
<212> TYPE: DNA
<213> ORGANISM: Artificial Sequence
<220> FEATURE:
<223> OTHER INFORMATION: Synthetic sequence

<400> SEQUENCE: 25
tggggcttct tgtttcagct gaaatagctt ataccagttg atcaata        47

<210> SEQ ID NO 26
<211> LENGTH: 43
<212> TYPE: DNA
<213> ORGANISM: Artificial Sequence
<220> FEATURE:
<223> OTHER INFORMATION: Synthetic sequence

<400> SEQUENCE: 26
tggggcttct tgtttcagct gagcttatac cagttgatca ata            43

<210> SEQ ID NO 27
<211> LENGTH: 42
<212> TYPE: DNA
<213> ORGANISM: Artificial Sequence
<220> FEATURE:
<223> OTHER INFORMATION: Synthetic sequence

<400> SEQUENCE: 27
tggggcttct tgtttcagct gacttatacc agttgatcaa ta             42

<210> SEQ ID NO 28
<211> LENGTH: 41
<212> TYPE: DNA
<213> ORGANISM: Artificial Sequence
<220> FEATURE:
<223> OTHER INFORMATION: Synthetic sequence

<400> SEQUENCE: 28
tggggcttct tgtttcagct gcttatacca gttgatcaat a              41

<210> SEQ ID NO 29
<211> LENGTH: 13
<212> TYPE: DNA
<213> ORGANISM: Artificial Sequence
<220> FEATURE:
<223> OTHER INFORMATION: Synthetic sequence

<400> SEQUENCE: 29
tggggcttct tgt                                             13

<210> SEQ ID NO 30
<211> LENGTH: 11
<212> TYPE: DNA
<213> ORGANISM: Artificial Sequence
<220> FEATURE:
<223> OTHER INFORMATION: Synthetic sequence

<400> SEQUENCE: 30
gttgatcaat a                                               11
```